United States Patent [19]

Baker

[11] 4,090,642

[45] May 23, 1978

[54] PACKAGE AND DISPENSER FOR FLOWABLE MATERIALS

[75] Inventor: Hugh William Barnes Baker, Beaconsfield, England

[73] Assignee: The Gillette Company, Boston, Mass.

[21] Appl. No.: 717,338

[22] Filed: Aug. 24, 1976

[30] Foreign Application Priority Data

Aug. 28, 1975 United Kingdom ............... 35579/75

[51] Int. Cl.² ...................... B65D 35/22; B65D 35/28; B65D 47/10; B65D 25/08
[52] U.S. Cl. ...................................... 222/94; 206/221; 206/484; 222/103; 222/541
[58] Field of Search ...................... 222/80, 81, 87, 107, 222/491, 541, 94, 103; 206/498, 531, 532, 219, 221, 484; 401/132, 134, 135; 354/303, 304; 221/25

[56] References Cited

U.S. PATENT DOCUMENTS

| | | | |
|---|---|---|---|
| 3,190,499 | 6/1965 | Dow | 206/498 X |
| 3,221,942 | 12/1965 | Glass | 206/498 X |
| 3,249,031 | 5/1966 | Gold | 222/81 |
| 3,250,202 | 5/1966 | Gold et al. | 354/304 |
| 3,441,353 | 4/1969 | Claff | 401/132 |
| 3,707,945 | 1/1973 | Boone | 118/234 |
| 3,777,647 | 12/1973 | Land | 354/304 |

Primary Examiner—Robert B. Reeves
Assistant Examiner—Francis J. Bartuska
Attorney, Agent, or Firm—Richard A. Wise; O. J. Bratlie; Wm. M. Anderson

[57] ABSTRACT

The present invention is concerned with (a) packages for flowable materials comprising a flexible laminated tape having two layers, a series of completely sealed pockets formed between the layers at intervals along the length of the tape and containing individual doses of material, and sealed openings in one of the layers through which the contents of the pockets can be discharged onto the surface of the tape by application of pressure to the tape and (b) dispensers for use with said packages.

4 Claims, 11 Drawing Figures

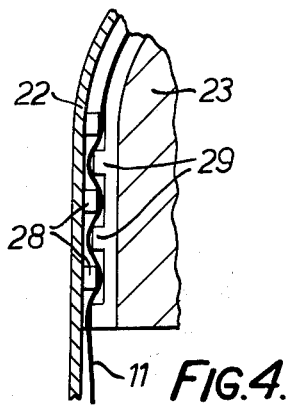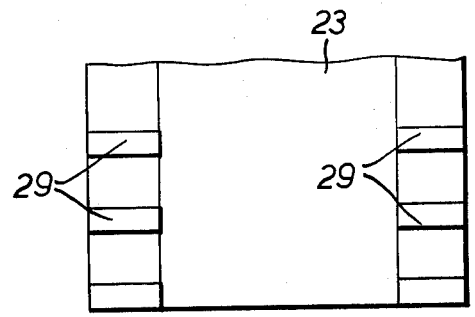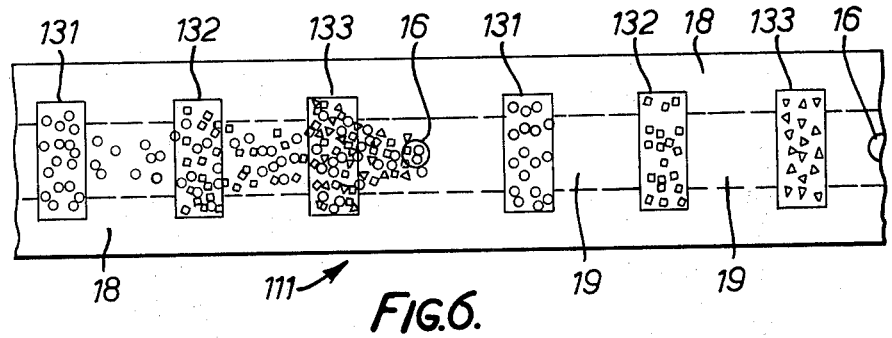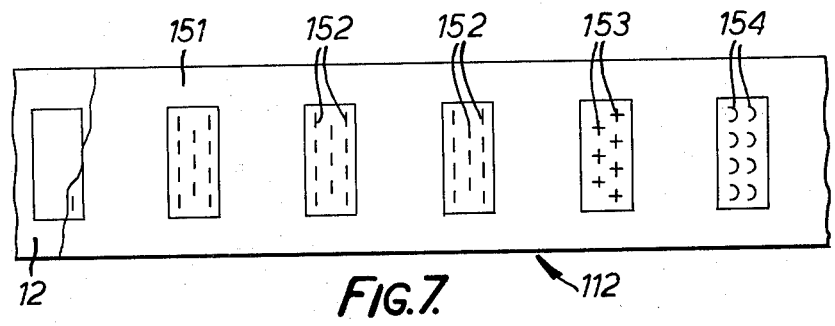

PACKAGE AND DISPENSER FOR FLOWABLE MATERIALS

This invention relates to the packaging and dispensing of flowable materials including liquids, creams, pastes, jellies, and powders.

In accordance with the invention there is provided a package of flowable material comprising a flexible laminated tape having two layers, a series of completely sealed pockets formed between the layers at intervals along the length of the tape and containing individual doses of material, and sealed openings in one of the layers through which the contents of the pockets can be discharged onto the surface of the tape by application of pressure to the tape.

While capable of application to a very wide variety of uses, the invention offers particular advantages when applied to the packaging of medical or cosmetic preparations intended for application to the skin. It can also be used with particular advantage for the packaging of materials comprising two or more ingredients which should not be mixed together until immediately before use.

Each pocket is completely sealed, both to prevent the premature escape of the packaged material and to protect it against atmospheric influence. The tape can be so constructed that by applying appropriate pressure to the tape the contents of the individual pockets can be exuded in turn onto the external surface of the tape and thus made available for use, or the contents of two or more adjacent pockets are mixed before being exuded onto the tape surface.

Some preferred embodiments of the invention are described below in detail with reference to the accompanying drawings, in which:

FIGS. 4 and 5 show a detail of the dispenser on an enlarged scale;

FIG. 6 is a view, corresponding to FIG. 1, of a modified form of tape;

FIG. 7 is a view, corresponding to FIG. 1, of another modified form of tape;

Figure 1:
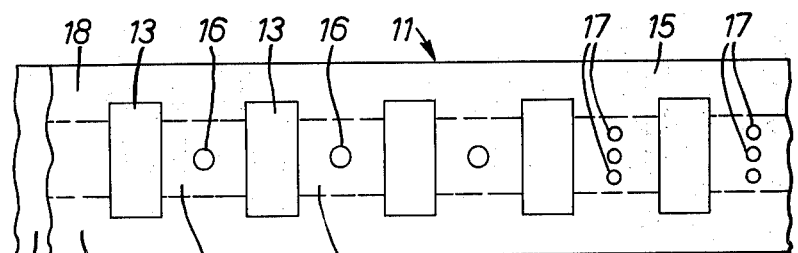
FIG. 1 is a plan view of one form of tape.
Figure 2:
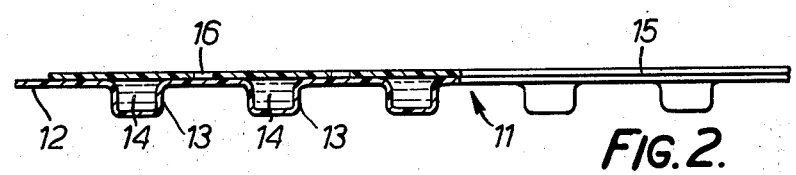
FIG. 2 is a side view, partly in section, of the tape of FIG. 1.

In making the tape 11 shown in FIGS. 1 and 2, a base strip 12 of a suitable plastics film or other material of appropriate width and indefinite length is embossed to form at intervals along its length substantially rectangular depressions or recesses 13, which extend across the major part of the width of the strip but terminate short of the margins thereof. Recesses of other forms can be used, as desired. The recesses are filled with individual doses of the material 14 to be disposed and a cover strip 15 is then applied to the base strip to enclose the doses in individual pockets. The cover strip 15, which is also made from a suitable plastics film or other material and has the same width as the base strip, if formed (at longitudinal intervals equal to the pitch of the recesses in the base strip) with punched holes, as shown at 16, or sets of punched holes, as shown at 17, the holes of each set being conveniently disposed on a line extending transversely of the strip. The two strips are registered so that the holes 16 or 17 in the cover strip lie above the parts of the base strip intermediate two adjacent recesses 13, preferably close to one of those recesses, and the strips are permanently sealed together along their marginal portions 18, while a peelable seal is formed between them over the areas 19 between the recesses in the base strip. Upon the application of a sufficient pressure to one of the pockets, the material 14 enclosed in it will penetrate between the strips, breaking the peelable seal between them, until it reaches the adjacent punched hole 16, or punched holes 17, in the cover strip, through which it escapes.

A length of tape of the character described above, or an individual pocket cut from such a tape, can be manipulated to discharge the contents of its pocket, or any one of its pockets, by means of the fingers alone, but still greater convenience is given by using such a tape with a suitable dispensing container, such as that now to be described.

Figure 3:
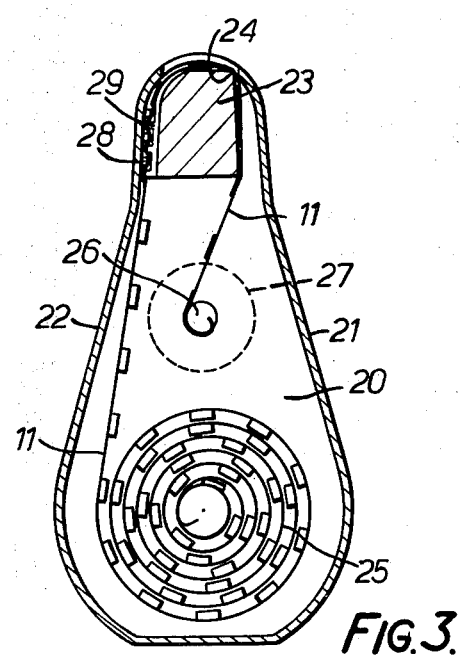
FIG. 3 is a sectional side view of a dispensing container for use with the tape of FIGS. 1 and 2.
Figure 8:
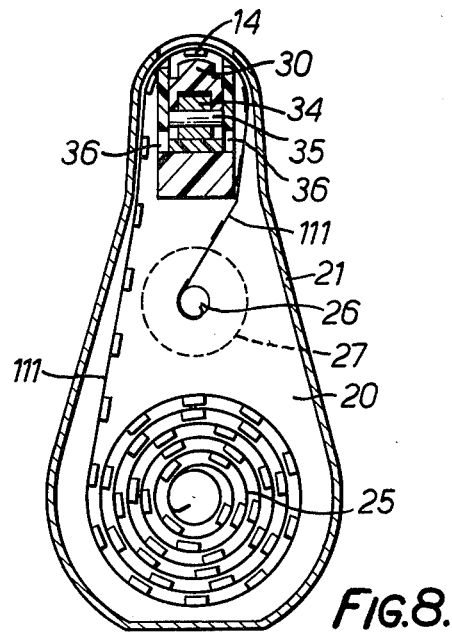
FIG. 8 is a sectional side view of an alternative form of dispensing container for use with the tape of FIG. 7.
Figure 9:
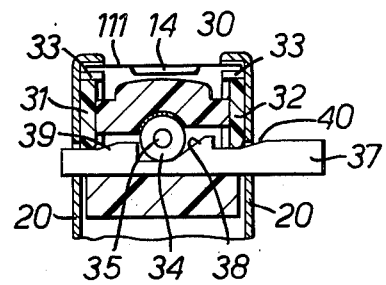
FIGS. 9, 10, and 11 are sectional views (taken at right angles to FIG. 8) of parts of this alternative dispenser in three different conditions of operaton.

The container illustrated in FIGS. 3 to 5 has parallel side walls 20, spaced apart at a distance slightly exceeding the width of the tape, and front and rear walls 21, 22 which are inclined upwardly towards one another and terminate short of the extreme top of the container. In the transverse aperture or opening thus formed there is mounted a fixed block 23 whose upper surface is so formed that a tape drawn forwardly over it will be turned through some 90° over a sharp edge at the front of the block. As illustrated, such an edge may be constituted simply by a corner 24 of the block, but it may be constituted by a ridge projecting from the block. The deeper lower part of the container accommodates a rolled-up length 25 of the tape 11 described above (the cover strip 15 being outermost) and the end of this length is led upwardly to the rear of the applicator block 23 and over that block. The tape then passes down at the front of the applicator block to a take-up spool 26 disposed between it and the storage roll, a knob 27 for rotating the take-up spool being provided externally of the container. As a tape of the construction described above is drawn forwardly over the edge formed on the block to bring one of the holes or sets of holes in the cover strip on to the upper surface of the block, the material in the pocket lying on the forward side of the hole or holes in question is progressively squeezed out of the pocket, between the superimposed strips of the tape and exuded through the holes, on to the exposed portion of the cover strip, from which it can then be transferred directly to the skin or other part which is to be treated with the materials. The surface applied to the skin is thus renewed at each operation, a fact which has important hygienic advantages.

To ensure that the tension in the tape as it passes over the sharp edge will be sufficient for extrusion of the material to be effected, the opposed surfaces of the container rear wall 22 and of the applicator block 23 between which the tape passes upwardly on its way to the dispensing position, may each be formed with parallel horizontal ribs and grooves which interengage with one another, so that the two marginal portions of the tape are constrained to follow undulating paths, thereby braking the tape and increasing the tension in it. This feature is best shown in FIGS. 4 and 5, FIG. 4 being a fragmentary sectional view of the dispenser taken in a plane parallel to that of FIG. 3, while FIG. 5 is a view, taken at right angles to FIG. 4, of the rear face of the applicator block 23 alone. It will be seen that the parts of the rear face of this block which engage the margins of the tape 11 are formed with spaced parallel ribs 29 which engage in the spaces between similar spaced ribs 28 formed on the inner face of the rear wall 22 of the casing, thus compelling the margins of tape 11 to follow an undulating path.

Alternatively, the applicator block, instead of being fixed, could be mounted to rock about a transverse axis and be so shaped that the pull applied to the tape by the take-up spool would rock the block about its axis and thereby squeeze the tape against the wall of the container.

When the material to be dispensed comprises two or more ingredients which should be kept separate from one another until required for use, the ingredients of each dose are separately loaded in alternating succession into adjacent recesses in the base strip and a hole (or a set of holes) is formed in the cover strip between each set of recesses only. A tape 111 of this character (for a three-ingredient material) is shown in FIG. 6. Pressure is applied first to the recess 131 furthest from the hole 16, so that its contents are displaced into (and mixed with the contents of) the adjacent recess 132, the mixture then passing through (and being admixed with the contents of) the remaining recess 133 in the set to the dispensing hole 16.

In another embodiment of the invention, illustrated in FIG. 7, a tape 112 comprises a base strip 12 of the same construction as in the embodiment first described and a cover strip 151 in which certain areas corresponding in size and position to the recesses in the base strip, are each formed with a multiplicity of openings in the form of small slits, which break the continuity of the film without removing any of its material. The slits can have a wide variety of forms including individual straight lines as shown at 152, pairs of lines crossing one another as shown at 153, and semi-circles as shown at 154. The two strips are brought into register with the slitted areas of the cover strip overlying the material-containing recesses of the base strip and the two strips are then permanently united together by fusion or adhesive over their two marginal portions and over the transversely extending portions lying between adjacent recesses, thus forming each recess into a separate completely closed pocket. The outer face of the cover strip 151 is coated with a frangible lacquer, thus sealing the slits in that strip. To dispense a dose of material from such a tape, one recessed portion of the base strip is pressed towards the cover strip so that the pressure on the material enclosed in the corresponding pocket rises sufficiently to break the coating of lacquer which holds the slits closed, thus allowing the material to exude through the slits on to the exposed surface of the cover strip, where it is available for application in any suitable manner.

A tape of the construction illustrated in FIG. 7 can be used with a dispensing container of the construction illustrated in FIGS. 8 to 11. This container is generally similar to the container described above with reference to FIGS. 3 to 5, but with the horizontal ribs 28 and 29 omitted and the fixed block 23 replaced by an applicator block 30 whose ends are guided for vertical sliding movement in a pair of clamp members 31, 32 which are themselves vertically slidable in grooves in the side walls 20 of the container and carry elastomer pads 33 on their upper ends. A part cylindrical groove in the underside of the applicator block 30 engages over a roller 34 of small diameter, supported by trunnions 35 engaged in vertical slots formed in webs 36 fast to the container and spaced inwardly from its front and rear walls 21, 22. A bar 37, extending transversely across the container below the roller 34, is formed with a cam surface 38 which, upon longitudinal movement of the bar, will either raise the roller 34 or allow it to drop and with a pair of cam surfaces 39, 40 of smaller rise which act similarly upon the clamp members 31, 32.

Figure 10:
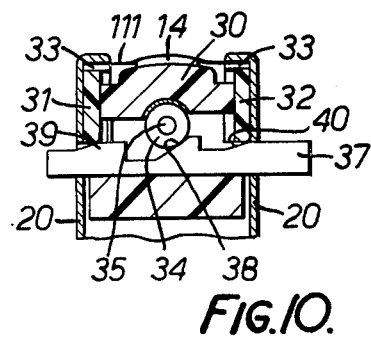
Figure 11:
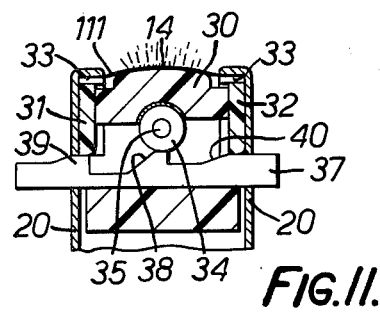

The tape 111 drawn from the storage coil 25 passes upwardly to the rear of the applicator block 30 and over that block, the margins of the tape passing between the pads 33 on the tops of the clamp members 31, 32 and the top wall of the casing. The tape then passes down in front of the applicator block to the take-up spool 26. The knob 27 is turned sufficiently to bring a full pocket 14 on to the upper surface of the applicator block, so that the portion of the cover strip 151 closing this pocket is exposed in the opening at the top of the container. The bar 37 is then shifted (to the left in FIG. 9) to raise the clamp members, roller, and applicator block. After the clamp members have been raised sufficiently for their elastomer pads to clamp the tape and hold it stationary, as shown in FIG. 10, the continued rise of the applicator block applies pressure to the pocket and exudes its contents, as shown in FIG. 11.

Dispensing containers generally similar to those described with reference to FIGS. 3 to 5 can also be used with a tape of the construction illustrated in FIG. 7, but in that case the sharp edge should be placed at the rear of the upper surface of the block, so that the material in a pocket will be squeezed out through the slits in the cover strip as that pocket is being brought forward into position on the upper surface of the block, where it is exposed through the opening in the casing.

Having thus described my invention, what I claim is:

1. A package for dispensing flowable materials in individual doses, said package comprising an elongated flexible tape comprising first and second layers, said tape having along its length a plurality of individual pockets containing the materials to be dispensed, said layers being permanently laminated to each other along the elongated margins of said tape, peelable areas beginning at the edge of said pockets and extending at least a portion of the distance to the adjacent pocket and openings in one of said layers over at least some of the peelable areas, whereby when pressure is applied to said pockets said material will penetrate through said peelable areas and flow out through said openings.

2. A package as defined in claim 1, wherein the materials in each pocket are discharged separately and the portion of said layer covering the peelable area adjacent each of said pockets is provided with an opening.

3. A package as defined in claim 1, wherein said tape contains sets of at least two adjacent pockets which contain materials to be mixed before being dispensed, said adjacent pockets containing said material to be mixed and being joined through peelable areas which are covered by portions of said layer without openings therein and the peelable area downstream of the last pocket in said set being covered by a portion of said layer with an opening therein.

4. A package for dispensing flowable materials in individual doses, in combination with a dispensing container therefor; said package comprising an elongated flexible tape comprising first and second layers, said tape having along its length a plurality of individual pockets containing the materials to be dispensed, said layers being permanently laminated to each other along the elongated margins of said tape, peelable areas beginning at the edge of said pockets and extending at least a portion of the distance to the adjacent pocket and openings in one of said layers over at least some of the peelable areas, whereby when pressure is applied to said pockets said material will penetrate through said peelable areas and flow out through said openings and said dispensing container comprising a housing having a dispensing opening therein, a rotatable roll mounted in said housing around which said tape is rolled, means for advancing said tape past the dispensing opening, means for applying pressure to said pockets in the region of said opening to force the contents of the pocket on to the surface of the tape and means for taking up the portion of the tape bearing the pockets whose contents have been dispensed.

* * * * *